(12) United States Patent
Safadi et al.

(10) Patent No.: US 8,178,127 B2
(45) Date of Patent: May 15, 2012

(54) STABLE LAQUINIMOD PREPARATIONS

(75) Inventors: Muhammad Safadi, Nazareth (IL); Daniella Licht, Givat Shmuel (IL); Ioana Lovinger, Kfar-Saba (IL); Aharon M. Eyal, Jerusalem (IL); Tomas Fristedt, Helsingborg (SE); Karl Jansson, Dalby (SE)

(73) Assignee: Teva Pharmaceuticals Industries, Ltd., Petach-Tikva (IL)

( * ) Notice: Subject to any disclaimer, the term of this patent is extended or adjusted under 35 U.S.C. 154(b) by 579 days.

(21) Appl. No.: 12/317,104

(22) Filed: Dec. 19, 2008

(65) Prior Publication Data
US 2009/0162432 A1 Jun. 25, 2009

Related U.S. Application Data

(60) Provisional application No. 61/008,698, filed on Dec. 20, 2007.

(51) Int. Cl.
*A61K 9/20* (2006.01)
(52) U.S. Cl. ........ 424/465; 514/312; 514/278; 424/474; 436/96; 548/486; 546/18
(58) Field of Classification Search ................ None
See application file for complete search history.

(56) References Cited

U.S. PATENT DOCUMENTS

| | | | |
|---|---|---|---|
| 3,024,257 A | 3/1962 | Millar et al. | |
| 4,107,310 A | 8/1978 | Allais et al. | |
| 4,547,511 A | 10/1985 | Eriksoo et al. | |
| 4,628,053 A | 12/1986 | Fries et al | |
| 4,738,971 A | 4/1988 | Eriksoo et al. | |
| 5,716,638 A | 2/1998 | Touitou | |
| 5,912,349 A | 6/1999 | Sih | |
| 6,077,851 A | 6/2000 | Bjork et al. | |
| 6,121,287 A | 9/2000 | Bjork et al. | |
| 6,133,285 A | 10/2000 | Bjork et al. | |
| 6,307,050 B1 | 10/2001 | Kwiatkowski et al. | |
| 6,395,750 B1 | 5/2002 | Hedlund et al. | |
| 6,593,343 B2 | 7/2003 | Bjork et al. | |
| 6,605,616 B1 | 8/2003 | Bjork et al. | |
| 6,802,422 B2 | 10/2004 | Kalvelage et al. | |
| 6,875,869 B2 | 4/2005 | Jansson | |
| 7,560,557 B2 | 7/2009 | Jansson | |
| 7,589,208 B2 | 9/2009 | Jansson et al. | |
| 2002/0173520 A1 | 11/2002 | Bjork et al. | |
| 2003/0087929 A1 | 5/2003 | Kimura et al. | |
| 2003/0119826 A1 | 6/2003 | Manning et al. | |
| 2003/0124187 A1 | 7/2003 | Mention et al. | |
| 2004/0247673 A1 | 12/2004 | Fergione et al. | |
| 2004/0253305 A1 | 12/2004 | Luner et al. | |
| 2005/0192315 A1 | 9/2005 | Jansson et al. | |
| 2005/0215586 A1 | 9/2005 | Jansson et al. | |
| 2005/0271717 A1 | 12/2005 | Berchielli et al. | |
| 2007/0088050 A1 | 4/2007 | Frenkel et al. | |
| 2007/0280891 A1 | 12/2007 | Tamarkin et al. | |
| 2007/0293537 A1 | 12/2007 | Patashnik et al. | |
| 2009/0232889 A1 | 9/2009 | Jansson et al. | |
| 2010/0055072 A1 | 3/2010 | Gant et al. | |
| 2011/0112141 A1 | 5/2011 | Frenkel et al. | |
| 2011/0118308 A1 | 5/2011 | Frenkel et al. | |

FOREIGN PATENT DOCUMENTS

| | | |
|---|---|---|
| EP | 0497740 | 8/1992 |
| EP | 1073639 | 11/2002 |
| EP | 1097139 | 12/2002 |
| EP | 1095021 | 9/2003 |
| EP | 1720531 | 11/2006 |
| EP | 1511732 | 12/2006 |
| WO | WO 90/15052 | 12/1990 |
| WO | WO 96/07601 | 3/1996 |
| WO | WO 99/55678 | 11/1999 |
| WO | WO 00/03991 | 1/2000 |
| WO | WO 00/03992 | 1/2000 |
| WO | WO/00/74654 | 2/2000 |
| WO | WO 01/30758 | 5/2001 |
| WO | WO 02/18343 | 3/2002 |
| WO | WO 03/106424 | 12/2003 |
| WO | WO 2005/041940 | 5/2005 |
| WO | WO 2005/074899 | 8/2005 |
| WO | WO 2007/047863 | 4/2007 |
| WO | WO 2007/146248 | 12/2007 |

OTHER PUBLICATIONS

21 CFR 211.116, Current Good Manufacturing Practice for Finished Pharmaceuticals, Stability Testing. 43 45077, Sep. 29, 1978, as amended at 46 FR 56412, Nov. 17, 1981. Entire section reproduced in the Office Action.*
PCT International Preliminary Report on Patentability issued Apr. 23, 2008 in connection with PCT International Application No. PCT/US2006/040925, filed Oct. 18, 2006.
PCT International Preliminary Report on Patentability issued Dec. 16, 2008 in connection with PCT International Application No. PCT/2007/013721, filed Jun. 12, 2007.
PCT International Search Report issued Apr. 26, 2007 in connection with PCT International Application No. PCT/US2006/040925, filed Oct. 18, 2006.
PCT International Search Report issued Oct. 23, 2008 in connection with PCT International Application No. PCT/US2007/013721, filed Jun. 12, 2007.
PCT International Search Report issued Feb. 20, 2009 in connection with PCT International Application No. PCT/US08/13890, filed Dec. 19, 2008.
Funiss, B et al. (1989) "Recrystallization Techniques" Vogel's Textbook of Practical Organic Chemistry, 5th ed., New York: John Wiley & Sons Inc.
Thompson, Claire "Investigating the Fundamentals of Drug Crystal . . . Microscopy" Thesis submitted to The University of Nottingham for the Degree of D.Phil, May 2003.

(Continued)

*Primary Examiner* — Bethany Barham
(74) *Attorney, Agent, or Firm* — John P. White; Cooper & Dunham LLP

(57) ABSTRACT

The subject invention provides a pharmaceutical composition comprising N-ethyl-N-phenyl-1,2,-dihydro-4-hydroxy-5-chloro-1-methyl-2-oxoquinoline-3-carboxamide or the salt thereof; a pharmaceutically acceptable carrier; and not more than 0.5% w/w relative to N-ethyl-N-phenyl-1,2,-dihydro-4-hydroxy-5-chloro-1-methyl-2-oxoquinoline-3-carboxamide of 2-Chloro-6-(1-ethyl-N-methyl-2-oxoindoline-3-carboxamido)benzoic acid, 1H,3H-spiro[5-chloro-1-methylquinoline-2,4-dione-3,3'-[1]ethylindolin-[2]-one], or 5-Chloro-N-ethyl-3-hydroxy-1-methyl-2,4-dioxo-N-phenyl-1,2,3,4-tetrahydro-quinoline-3-carboxamide.

16 Claims, No Drawings

OTHER PUBLICATIONS

PCT International Preliminary Report on Patentability issued Mar. 8, 2011 in connection with PCT International Application No. PCT/US2009/055692.

PCT International Search Report issued Apr. 21, 2010 in connection with PCT International Application No. PCT/2009/055692.

Written Opinion of the International Searching Authority issued Apr. 21, 2010 in connection with PCT International Application No. PCT/US2009/055692.

Nov. 12, 2010 Official Communication Pursuant to Article 94(3) EPC issued in connection with European Patent Application No. 07809468.7.

Jan. 17, 2011 Extended European Search Report issued in connection with European Patent Application No. 08864658.3.

Final Office Action issued by the U.S. PAtent and Trademark Office on Nov. 15, 2010 in connection with U.S. Appl. No. 11/811,810.

Advisory Action mailed Feb. 11, 2011 by the U.S. Patent and Trademark Office in connection with U.S. Appl. No. 11/811,810.

Advisory Action mailed Mar. 29, 2011 by the U.S. Patent and Trademark Office in conneciton with U.S. Appl. No. 11/811,810.

Notice of Allowance issued by the U.S. Patent and Trademark Office on Apr. 8, 2011 in connection with U.S. Appl. No. 11/811,810.

Jan. 14, 2011 Amendment Under 37 C.F.R. §1.116 in Response to Nov. 15, 2010 Final Office Action filed with the USPTO in conneciton with U.S. Appl. No. 11/811,810.

Mar. 15, 2011 Amendment Under 37 C.F.R. §1.116 in Response to Feb. 11, 2011 Advisory Action . . . filed with the USPTO in connection with U.S. Appl. No. 11/811,810.

Jan. 12, 2011 Response to Nov. 12, 2010 Communication Pursuant to Article 94 (3) EPC issued by the EPO in connection with European Patent Application No. 07809468.7.

Oct. 25, 2010 Response to Jun. 12, 2010 Office Action issued in connection with Chinese Patent App. No. 200780021677.1 (with English language draft sent to Chinese assoc.).

Jan. 21, 2011 Response to Sep. 21, 2010 Office Action issued in connection with Eurasian App. No. 200870599 (with English language draft sent to Eurasian assoc.).

Sandberg-Wollheim, et al. (2005) "48-Week Open Safety Study With A High-Dose . . . " Therapy- immunomodulation-Part II, Sep. 30, 2005, 15:30-17:00 (Abstract only).

Tuvesson et al. (2005) "Cytochrome P450 3A4 is the Major Enzyme Responsible for the Metabolism of Laquinimod . . . " Drug Metabolism and Disposition. 33(6):866-872.

Written Opinion of the International Searching Authority issued Apr. 26, 2007 in connection with PCT International Application No. PCT/US06/040925, filed Oct. 18, 2006.

Written Opinion of the International Searching Authority issued Oct. 23, 2008 in connection with PCT International Application No. PCT/US07/013721, filed Jun. 12, 2007.

Written Opinion of the International Searching Authority issued Feb. 20, 2009 in connection with PCT International Application No. PCT/US08/13890, filed Dec. 19, 2008.

Extended European Search Report issued Feb. 16, 2009 in connection with European Application No. 06826297.1 (Teva Pharmaceutical Industries, Ltd.).

Office Action issued by the U.S. Patent and Trademark Office on Oct. 16, 2008 in connection with U.S. Appl. No. 11/583,282.

U.S. Appl. No. 12/804,795, filed Jul. 29, 2010, Tarcic et al.

U.S. Appl. No. 12/803,121, filed Jun. 18, 2010, Tarcic et al.

U.S. Appl. No. 12/806,275, filed Aug. 9, 2010, Liat Hayardeny.

PCT International Preliminary Report on Patentability issued Jun. 22, 2010 in connection with PCT International Application No. PCT/US08/13890, filed Dec. 19, 2008.

Supplementary European Search Report issued Aug. 5, 2009 in connection with European Application No. 07809468.7.

Extended European Search Report issued Aug. 24, 2009 in connection with European Application No. 07809468.7.

Communication Pursuant to Article 94(3) EPC issued Dec. 15, 2009 in connection with European Application No. 07809468.7.

May 7, 2010 Official Communication Pursuant to Article 94(3) EPC issued in connection with European Patent Application No. 07809468.7.

Jul. 2, 2010 Examination Report issued by the New Zealand Patent Office in connection with New Zealand Patent Application No. 573846.

Jun. 12, 2010 Office Action issued by the Chinese Patent Office in connection with Chinese Application No. 200780021677.1 (with English translation).

Sep. 21, 2010 Office Action issued by the Eurasian Patent Office in connection with Eurasian Application No. 200870599 (with English translation).

Office Action issued by the U.S. Patent and Trademark Office on Aug. 24, 2009 in connection with U.S. Appl. No. 11/811,810.

Office Action issued by the U.S. Patent and Trademark Office on Jul. 21, 2010 in connection with U.S. Appl. No. 11/811,810.

Sep. 11, 2009 Communication in Response to Aug. 24, 2009 Office Action in connection with U.S. Appl. No. 11/811,810.

Apr. 6, 2010 Amendment in Response to Jan. 6, 2010 Office Action in connection with U.S. Appl. No. 11/811,810.

Jan. 13, 2010 Response to Dec. 15, 2009 Office Action issued by the European Patent Office in connection with European Patent Application No. 07809468.7-2123.

Apr. 15, 2011 Office Action issued by the Ukrainian Patent Office in connection with Ukrainian Patent Application No. 1200930145, filed Jan. 9, 2008 (with Eng. Trans.).

"Note For Guidance on Stability Testing: Stability Testing of New Drug Substances and Products" European Medicines Agency, Aug. 2003.

\* cited by examiner

STABLE LAQUINIMOD PREPARATIONS

This application claims the benefit of U.S. Provisional Application No. 61/008,698, filed Dec. 20, 2007, the entire content of which is hereby incorporated by reference herein.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

Laquinimod is a compound which has been shown to be effective in the acute experimental autoimmune encephalomyelitis (aEAE) model (U.S. Pat. No. 6,077,851). Its chemical name is N-ethyl-N-phenyl-1,2-dihydro-4-hydroxy-5-chloro-1-methyl-2-oxoquinoline-3-carboxamide, and its Chemical Registry number is 248281-84-7. The processes of synthesis of laquinimod and the preparation of its sodium salt are disclosed in U.S. Pat. No. 6,077,851. An additional process of synthesis of laquinimod is disclosed in U.S. Pat. No. 6,875,869.

Pharmaceutical compositions comprising laquinimod sodium are disclosed in PCT International Application Publication No. WO 2005/074899.

SUMMARY OF THE INVENTION

The subject invention provides a pharmaceutical composition comprising N-ethyl-N-phenyl-1,2,-dihydro-4-hydroxy-5-chloro-1-methyl-2-oxoquinoline-3-carboxamide or a pharmaceutically acceptable salt thereof, oxidation reducing agent, and a pharmaceutically acceptable carrier.

The subject invention also provides a sealed package comprising the pharmaceutical composition described herein or a pharmaceutically acceptable salt thereof and an oxygen absorbing agent.

The subject invention also provides a process for the manufacture of a sealed package comprising a pharmaceutical composition of N-ethyl-N-phenyl-1,2,-dihydro-4-hydroxy-5-chloro-1-methyl-2-oxoquinoline-3-carboxamide or a pharmaceutically acceptable salt thereof comprising preparing a pharmaceutical composition comprising N-ethyl-N-phenyl-1,2,-dihydro-4-hydroxy-5-chloro-1-methyl-2-oxoquinoline-3-carboxamide or a pharmaceutically acceptable salt thereof and packaging said pharmaceutical composition in a container under environmental conditions containing less oxygen than standard atmospheric conditions.

The subject invention also provides a pharmaceutical formulation in tablet form wherein the tablet comprises a core comprising N-ethyl-N-phenyl-1,2,-dihydro-4-hydroxy-5-chloro-1-methyl-2-oxoquinoline-3-carboxamide or a pharmaceutically acceptable salt thereof and a pharmaceutically acceptable carrier and a coating which inhibits oxygen from contacting the core.

The subject invention also provides a process for validating a batch of a pharmaceutical product containing N-ethyl-N-phenyl-1,2,-dihydro-4-hydroxy-5-chloro-1-methyl-2-oxoquinoline-3-carboxamide or a salt thereof and a pharmaceutically acceptable carrier for distribution.

The subject invention also provides a process for validating a batch of N-ethyl-N-phenyl-1,2,-dihydro-4-hydroxy-5-chloro-1-methyl-2-oxoquinoline-3-carboxamide or a salt thereof for distribution.

The subject invention also provides a process for preparing a pharmaceutical product comprising N-ethyl-N-phenyl-1,2,-dihydro-4-hydroxy-5-chloro-1-methyl-2-oxoquinoline-3-carboxamide or a salt thereof and a pharmaceutically acceptable carrier, wherein the pharmaceutical product has not more than a total of 0.5% w/w relative to N-ethyl-N-phenyl-1,2,-dihydro-4-hydroxy-5-chloro-1-methyl-2-oxoquinoline-3-carboxamide of the oxidation decomposition products 2-Chloro-6-(1-ethyl-N-methyl-2-oxoindoline-3-carboxamido)benzoic acid, 1H,3H-spiro[5-chloro-1-methylquinoline-2,4-dione-3,3'-[1]ethylindolin-[2]-one], and 5-Chloro-N-ethyl-3-hydroxy-1-methyl-2,4-dioxo-N-phenyl-1,2,3,4-tetrahydro-quinoline-3-carboxamide.

The subject invention also provides a process for testing whether a sample contains an undesirable oxidation decomposition products of 2-Chloro-6-(1-ethyl-N-methyl-2-oxoindoline-3-carboxamido)benzoic acid, 1H,3H-spiro[5-chloro-1-methylquinoline-2,4-dione-3,3'-[1]ethylindolin-[2]-one], or 5-Chloro-N-ethyl-3-hydroxy-1-methyl-2,4-dioxo-N-phenyl-1,2,3,4-tetrahydro-quinoline-3-carboxamide.

The subject invention also provides an isolated compound having the structure:

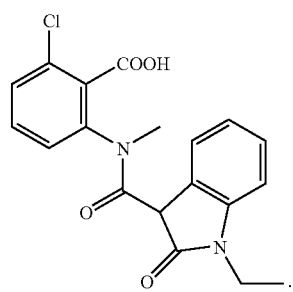

I

The subject invention also provides an isolated compound having the structure:

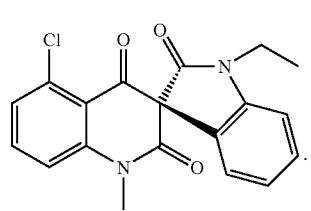

II

DETAILED DESCRIPTION OF THE INVENTION

The subject invention provides a pharmaceutical composition comprising N-ethyl-N-phenyl-1,2,-dihydro-4-hydroxy-5-chloro-1-methyl-2-oxoquinoline-3-carboxamide or a pharmaceutically acceptable salt thereof, oxidation reducing agent, and a pharmaceutically acceptable carrier.

In an embodiment of the pharmaceutical composition the N-ethyl-N-phenyl-1,2,-dihydro-4-hydroxy-5-chloro-1-methyl-2-oxoquinoline-3-carboxamide is in the form of a pharmaceutically acceptable salt.

In another embodiment of the pharmaceutical composition, the pharmaceutically acceptable salt of N-ethyl-N-phenyl-1,2,-dihydro-4-hydroxy-5-chloro-1-methyl-2-oxoquinoline-3-carboxamide is a lithium salt, a sodium salt or a calcium salt.

In another embodiment of the pharmaceutical composition, the pharmaceutically acceptable salt of N-ethyl-N-phenyl-1,2,-dihydro-4-hydroxy-5-chloro-1-methyl-2-oxoquinoline-3-carboxamide is N-ethyl-N-phenyl-1,2,-dihydro-4-hydroxy-5-chloro-1-methyl-2-oxoquinoline-3-carboxamide sodium.

In an embodiment, the pharmaceutical composition is in solid form.

In another embodiment, the pharmaceutical composition is characterized in that 1.0% or less of the of N-ethyl-N-phenyl-1,2,-dihydro-4-hydroxy-5-chloro-1-methyl-2-oxoquinoline-3-carboxamide or of the pharmaceutically acceptable salt thereof degrades upon exposure to a 0.15% $H_2O_2$ solution for 40 minutes.

In yet another embodiment, the pharmaceutical composition is free of oxidation decomposition products of N-ethyl-N-phenyl-1,2,-dihydro-4-hydroxy-5-chloro-1-methyl-2-oxoquinoline-3-carboxamide.

In yet another embodiment, the pharmaceutical composition contains an undetectable amount of oxidation decomposition products of N-ethyl-N-phenyl-1,2,-dihydro-4-hydroxy-5-chloro-1-methyl-2-oxoquinoline-3-carboxamide.

In yet another embodiment, the pharmaceutical composition contains less than 1% by weight of oxidation decomposition products of N-ethyl-N-phenyl-1,2,-dihydro-4-hydroxy-5-chloro-1-methyl-2-oxoquinoline-3-carboxamide.

In yet another embodiment, the pharmaceutical composition is free of 2-Chloro-6-(1-ethyl-N-methyl-2-oxoindoline-3-carboxamido)benzoic acid, 1H,3H-spiro[5-chloro-1-methylquinoline-2,4-dione-3,3'-[1]ethylindolin-[2]-one], and 5-Chloro-N-ethyl-3-hydroxy-1-methyl-2,4-dioxo-N-phenyl-1,2,3,4-tetrahydro-quinoline-3-carboxamide.

In yet another embodiment, the pharmaceutical composition contains not more than 0.5% w/w relative to N-ethyl-N-phenyl-1,2,-dihydro-4-hydroxy-5-chloro-1-methyl-2-oxoquinoline-3-carboxamide of 2-Chloro-6-(1-ethyl-N-methyl-2-oxoindoline-3-carboxamido)benzoic acid, 1H,3H-spiro[5-chloro-1-methylquinoline-2,4-dione-3,3'-[1]ethylindolin-[2]-one], or 5-Chloro-N-ethyl-3-hydroxy-1-methyl-2,4-dioxo-N-phenyl-1,2,3,4-tetrahydro-quinoline-3-carboxamide.

The subject invention also provides a sealed package comprising the pharmaceutical composition described herein or a pharmaceutically acceptable salt thereof and an oxygen absorbing agent.

In an embodiment of the sealed package, the oxygen absorbing agent is iron.

The subject invention also provides a process for the manufacture of a sealed package comprising a pharmaceutical composition of N-ethyl-N-phenyl-1,2,-dihydro-4-hydroxy-5-chloro-1-methyl-2-oxoquinoline-3-carboxamide or a pharmaceutically acceptable salt thereof comprising preparing a pharmaceutical composition comprising a pharmaceutical composition of N-ethyl-N-phenyl-1,2,-dihydro-4-hydroxy-5-chloro-1-methyl-2-oxoquinoline-3-carboxamide or a pharmaceutically acceptable salt thereof and packaging said pharmaceutical composition in a container under environmental conditions containing less oxygen than standard atmospheric conditions.

The subject invention also provides a pharmaceutical formulation in tablet form wherein the tablet comprises a core comprising N-ethyl-N-phenyl-1,2,-dihydro-4-hydroxy-5-chloro-1-methyl-2-oxoquinoline-3-carboxamide or a pharmaceutically acceptable salt thereof and a pharmaceutically acceptable carrier and a coating which inhibits oxygen from contacting the core.

In one embodiment, the coating comprises a cellulosic polymer, a detackifier, a gloss enhancer, and pigment. A detackifier is a substance added to a screen printing ink as a means of reducing its stickiness, or tack, and improve the ink's flow characteristics. Examples of detackifiers are lecithins, stearic acid, polysorbates, glyceryl monostearate, sodium lauryl sulfate, poloxamers, monoglycerides, diglycerides and mixtures thereof. In an embodiment, the coating is Opadry®fx™, manufactured by Colorcon, West Point, Pa., USA. Opadry®fx™ is described in U.S. Pat. No. 6,902,609, the entire content of which is hereby incorporated by reference herein.

Opadry®fx™ is a pearlescent film coating system which has been found to have excellent oxygen barrier properties compared to other tablet film coating systems. In one study, Opadry®fx™ was found to inhibit oxidation of ibuprofen at various temperatures by acting as an oxygen barrier. The oxidation rate of ibuprofen coated with Opadry®fx™ was found to be very slow and difficult to quantify even at high temperatures (60° C.). (Gulian et al., "Oxidative Protection of Ibuprofen Using Opadry®fx™ Special Effects Film Coating System" *American Academy of Pharmaceutical Scientists*, November, 2004).

In addition, Opadry®fx™ was found to provide oxidative protection from stressed illumination conditions. Gulian et al. compared degradation product profiles for uncoated ibuprofen tablets, tablets coated with hydroxypropylmethylcellulose (HPMC)/$TiO_2$ and tablets coated with Opadry®fx™ in stressed UV and visible light conditions. The results showed that tablets coated with Opadry®fx™ have the lowest amount of degradants. This study strongly suggests that the primary photolytic degradation pathways are oxidative in nature. Since oxygen is an essential co-reactant during these photolytic degradation processes, the low oxygen permeability of Opadry®fx™ results in lower levels of degradants. (Gulian et al.)

The coating may also comprise Opaglos®2 (manufactured by Colorcon, West Point, Pa., USA), hydroxypropylmethylcellulose (HPMC), or titanium dioxide.

The subject invention also provides a process for validating a batch of a pharmaceutical product containing N-ethyl-N-phenyl-1,2,-dihydro-4-hydroxy-5-chloro-1-methyl-2-oxoquinoline-3-carboxamide or a salt thereof and a pharmaceutically acceptable carrier for distribution comprising a) subjecting a sample of the batch to stability testing;
b) determining the total amount of an oxidation decomposition product in the sample of the batch after stability testing; and
c) validating the batch for distribution only if the sample of the batch after stability testing contains not more than a total of 0.5% w/w relative to N-ethyl-N-phenyl-1,2,-dihydro-4-hydroxy-5-chloro-1-methyl-2-oxoquinoline-3-carboxamide of the oxidation decomposition products 2-Chloro-6-(1-ethyl-N-methyl-2-oxoindoline-3-carboxamido)benzoic acid, 1H,3H-spiro[5-chloro-1-methylquinoline-2,4-dione-3,3'-[1]ethylindolin-[2]-one], and 5-Chloro-N-ethyl-3-hydroxy-1-methyl-2,4-dioxo-N-phenyl-1,2,3,4-tetrahydro-quinoline-3-carboxamide.

In an embodiment of the process, wherein the oxidation decomposition product is 2-Chloro-6-(1-ethyl-N-methyl-2-oxoindoline-3-carboxamido)benzoic acid, 5-Chloro-N-ethyl-3-hydroxy-1-methyl-2,4-dioxo-N-phenyl-1,2,3,4-tetrahydro-quinoline-3-carboxamide or 1H,3H-spiro[5-chloro-1-methylquinoline-2,4-dione-3,3'-[1]ethylindolin-[2]-one], or a mixture thereof.

In another embodiment of the process, wherein in the step (b), the amount is determined using a measurement of mass, ultraviolet absorption, refractive index, ionization or voltammogram.

The subject invention also provides a process for validating a batch of N-ethyl-N-phenyl-1,2,-dihydro-4-hydroxy-5-chloro-1-methyl-2-oxoquinoline-3-carboxamide or a salt thereof for distribution comprising
 a) subjecting a sample of the batch to stability testing;
 b) determining the total amount of an oxidation decomposition product in the sample of the batch after stability testing; and
 c) validating the batch for distribution only if the sample of the batch after stability testing contains not more than a total of 0.1% w/w relative to N-ethyl-N-phenyl-1,2,-dihydro-4-hydroxy-5-chloro-1-methyl-2-oxoquinoline-3-carboxamide of the oxidation decomposition products 2-Chloro-6-(1-ethyl-N-methyl-2-oxoindoline-3-carboxamido)benzoic acid, 1H,3H-spiro[5-chloro-1-methylquinoline-2,4-dione-3,3'-[1]ethylindolin-[2]-one], and 5-Chloro-N-ethyl-3-hydroxy-1-methyl-2,4-dioxo-N-phenyl-1,2,3,4-tetrahydro-quinoline-3-carboxamide.

In an embodiment of the process, wherein the oxidation decomposition product is 2-Chloro-6-(1-ethyl-N-methyl-2-oxoindoline-3-carboxamido)benzoic acid, 5-Chloro-N-ethyl-3-hydroxy-1-methyl-2,4-dioxo-N-phenyl-1,2,3,4-tetrahydro-quinoline-3-carboxamide or 1H,3H-spiro[5-chloro-1-methylquinoline-2,4-dione-3,3'-[1]ethylindolin-[2-one], or a mixture thereof.

In another embodiment of the process, wherein in the step (b), the amount is determined using a measurement of mass, ultraviolet absorption, refractive index, ionization or voltammogram.

The subject invention also provides a process for preparing a pharmaceutical product comprising N-ethyl-N-phenyl-1,2,-dihydro-4-hydroxy-5-chloro-1-methyl-2-oxoquinoline-3-carboxamide or a salt thereof and a pharmaceutically acceptable carrier, wherein the pharmaceutical product has not more than a total of 0.5% w/w relative to N-ethyl-N-phenyl-1,2,-dihydro-4-hydroxy-5-chloro-1-methyl-2-oxoquinoline-3-carboxamide of the oxidation decomposition products 2-Chloro-6-(1-ethyl-N-methyl-2-oxoindoline-3-carboxamido)benzoic acid, 1H,3H-spiro[5-chloro-1-methylquinoline-2,4-dione-3,3'-[1]ethylindolin-[2]-one], and 5-Chloro-N-ethyl-3-hydroxy-1-methyl-2,4-dioxo-N-phenyl-1,2,3,4-tetrahydro-quinoline-3-carboxamide, comprising
 a) obtaining a batch of N-ethyl-N-phenyl-1,2,-dihydro-4-hydroxy-5-chloro-1-methyl-2-oxoquinoline-3-carboxamide or a salt thereof;
 b) determining the total amount of N-ethyl-N-phenyl-1,2,-dihydro-4-hydroxy-5-chloro-1-methyl-2-oxoquinoline-3-carboxamide or a salt thereof present in the batch; and
 c) preparing the pharmaceutical product from the batch only if the batch is determined to have not more than a total of 0.5% w/w relative to N-ethyl-N-phenyl-1,2,-dihydro-4-hydroxy-5-chloro-1-methyl-2-oxoquinoline-3-carboxamide of the oxidation decomposition products 2-Chloro-6-(1-ethyl-N-methyl-2-oxoindoline-3-carboxamido)benzoic acid, 1H,3H-spiro[5-chloro-1-methylquinoline-2,4-dione-3,3'-[1]ethylindolin-[2]-one], and 5-Chloro-N-ethyl-3-hydroxy-1-methyl-2,4-dioxo-N-phenyl-1,2,3,4-tetrahydro-quinoline-3-carboxamide.

The subject invention also provides a process for testing whether a sample contains an undesirable oxidation decomposition products of 2-Chloro-6-(1-ethyl-N-methyl-2-oxoindoline-3-carboxamido)benzoic acid, 1H,3H-spiro[5-chloro-1-methylquinoline-2,4-dione-3,3'-[1]ethylindolin-[2]-one], or 5-Chloro-N-ethyl-3-hydroxy-1-methyl-2,4-dioxo-N-phenyl-1,2,3,4-tetrahydro-quinoline-3-carboxamide which comprises determining whether the sample contains a compound having the structure:

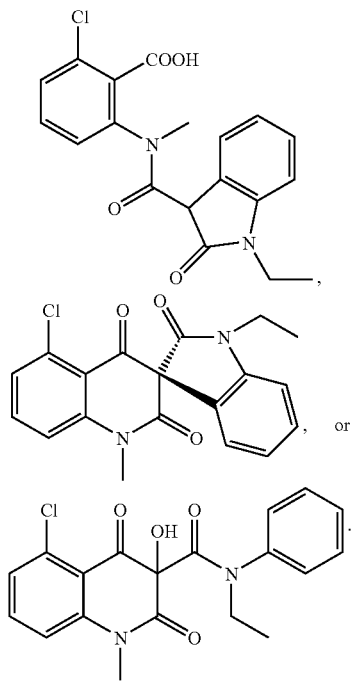

The subject invention also provides an isolated compound having the structure:

I

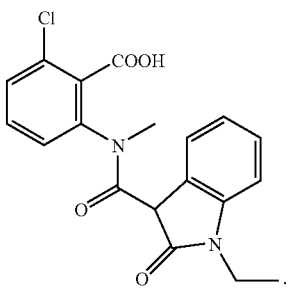

The subject invention also provides an isolated compound having the structure:

II

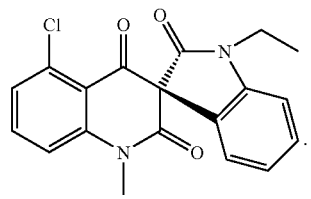

Every embodiment of the invention is contemplated as being employed with every other disclosed embodiment. For example, the pharmaceutical composition disclosed can be packaged in the sealed package disclosed, and such combination can be manufactured by the disclosed processes and methods.

Many of the prior art formulations of Laquinimod relate to formulations comprising alkaline agents and meglumine. Both of these excipients have been found to be incompatible with certain coloring agents in capsules, as capsule spotting was detected in various capsules. This was attributed to the alkalinity of the formulation. An advantage of the formulations provided herein is the stability and compatibility with many types of colors.

As used herein, "oxidation reducing agent" refers to a group of chemicals which includes an "antioxidant", a "reduction agent" and a "chelating agent".

As used herein, "antioxidant" refers to a compound selected from the group consisting of tocopherol, methionine, glutathione, tocotrienol, dimethyl glycine, betaine, butylated hydroxyanisole, butylated hydroxytoluene, turmerin, vitamin E, ascorbyl palmitate, tocopherol, deteroxime mesylate, methyl paraben, ethyl paraben, butylated hydroxyanisole, butylated hydroxytoluene, propyl gallate, sodium or potassium metabisulfite, sodium or potassium sulfite, alpha tocopherol or derivatives thereof, sodium ascorbate, disodium edentate, BHA (butylated hydroxyanisole), a pharmaceutically acceptable salt or ester of the mentioned compounds, and mixtures thereof.

The term "antioxidant" as used herein also refers to Flavonoids such as those selected from the group of quercetin, morin, naringenin and hesperetin, taxifolin, afzelin, quercitrin, myricitrin, genistein, apigenin and biochanin A, flavone, flavopiridol, isoflavonoids such as the soy isoflavonoid, genistein, catechins such as the tea catechin epigallocatechin gallate, flavonol, epicatechin, hesperetin, chrysin, diosmin, hesperidin, luteolin, and rutin.

As used herein, "reduction agent" refers to a compound selected from the group consisting of thiol-containing compound, thioglycerol, mercaptoethanol, thioglycol, thiodiglycol, cysteine, thioglucose, dithiothreitol (DTT), dithio-bis-maleimidoethane (DTME), 2,6-di-tert-butyl-4-methylphenol (BHT), sodium dithionite, sodium bisulphite, formamidine sodium metabisulphite, and ammonium bisulphite."

As used herein, "chelating agent" refers to a compound selected from the group consisting of penicillamine, trientine, N,N'-diethyldithiocarbamate (DDC), 2,3,2'-tetraamine(2,3,2'-tet), neocuproine, N,N,N',N'-tetrakis(2-pyridylmethyl)ethylenediamine (TPEN), 1,10-phenanthroline (PHE), tetraethylenepentamine, triethylenetetraamine and tris(2-carboxyethyl)phosphine (TCEP), ferrioxamine, CP94, EDTA, deferoxainine B (DFO) as the methanesulfonate salt (also known as desferrioxanilne B mesylate (DFOM)), desferal from Novartis (previously Ciba-Giegy), and apoferritin.

The terms "antioxidant", "reduction agent" and "chelating agents" as used herein each exclude meglumine.

As used herein, "oxygen absorbing agent" refers to a compound selected from the group consisting of thiol-containing compound, thioglycerol, mercaptoethanol, thioglycol, thiodiglycol, cysteine, thioglucose, dithiothreitol (DTT), dithio-bis-maleimidoethane (DTME), vitamin B, vitamin C, 2,6-di-tert-butyl-4-methylphenol (BHT), sodium dithionite, sodium bisulphite, stannous ion, iron, copper, nickel, tin, zinc, a stannous salt such as stannous chloride or stannous tartrate, sulphur dioxide, sodium metabisulphite, and ammonium bisulphite.

EXPERIMENTAL DETAILS

Example 1

Laquinimod Sodium Capsules Comprising Sodium Carbonate

Capsules were made which corresponded to 0.3 mg of laquinimod acid (LA) per capsule and 0.6 mg of laquinimod acid per capsule using the following excipients as shown in Table 1:

TABLE 1

| Component | 0.3 mg LA/capsule | 0.6 mg LA/capsule |
| --- | --- | --- |
| Laquinimod Sodium | 0.32 | 0.64 |
| Mannitol USP | 151.08 | 302.16 |
| Sodium carbonate anhydrous USP | 4.55 | 9.10 |
| Sodium Stearyl fumarate NF | 1.6 | 3.2 |
| Total Weight | 157.55 | 315.1 |

The capsules were made using the following steps:
1. Mannitol and 99% of the total desired anhydrous sodium carbonate were placed into a high shear granulating mixer and were mixed for 30 seconds.
2. A solution of laquinimod sodium, 1% of the total desired anhydrous sodium carbonate and purified water was prepared in a mixer until dissolved.
3. The solution from step 2 was added to the contents of the high shear granulating mixer of step 1 and was mixed to form a suitable granulate.
4. The granulate was dried in a fluid bed dryer with the inlet air temperature of 50° C. and outlet air temperature of 40° C.
5. The dry granulate was milled using a 0.8 mm screen, and blended with sodium stearyl fumarate.
6. The mixture from step 5 was filled into size 1 hard gelatin capsules (0.5 mL volume) for the 0.6 mg laquinimod acid dose and into size 3 hard gelatin capsules (0.3 mL volume) for the 0.3 mg of laquinimod acid dose.

Example 2a

Laquinimod Sodium Capsules Comprising Meglumine

Capsules were made which corresponded to 0.3 mg of laquinimod acid (LA) per capsule and 0.6 mg of laquinimod acid per capsule using the following excipients as shown in Table 2:

TABLE 2

| Component | 0.3 mg LA/capsule | 0.6 mg LA/capsule |
| --- | --- | --- |
| Laquinimod Sodium | 0.32 | 0.64 |
| Mannitol USP | 151.08 | 302.16 |
| Meglumine USP | 5.0 | 10.0 |
| Sodium Stearyl fumarate NF | 1.6 | 3.2 |
| Total Weight | 158 | 316 |

The capsules were made using the following steps:
1. Mannitol and 90% of the total desired meglumine were placed into a high shear granulating mixer and were mixed for 30 seconds.

2. A solution of laquinimod sodium, 10% of the total desired meglumine and purified water was prepared in a mixer until dissolved.
3. The solution from step 2 was added to the contents of the high shear granulating mixer of step 1 and mixed to form a suitable granulate.
4. The granulate was dried in a fluid bed dryer with the inlet air temperature of 50° C. and outlet air temperature of 40° C.
5. The dry granulate was milled using a 0.8 mm screen, and blended with sodium stearyl fumarate.
6. The mixture from step 5 was filled into size 1 hard gelatin capsules (0.5 mL volume) for the 0.6 mg laquinimod acid dose and into size 3 hard gelatin capsules (0.3 mL volume) for the 0.3 mg of laquinimod acid dose.

Example 2b

Laquinimod Sodium Tablets Comprising Meglumine

Laquinimod sodium tablets were prepared using the same excipients as in table 2 and using the same procedure as in steps 1-5 of example 2a. After step 5, the blend was transferred into a tabletation machine and punched. The tablets were tested for average weight, individual weight, thickness, hardness, friability and disintegration.

Example 3

Forced Degradation of Laquinimod Sodium Capsules

Laquinimod sodium capsules manufactured according to Examples 1 and 2 were exposed to 0.15% $H_2O_2$ solution for 40 minutes.

The amount of sodium laquinimod in each capsule after exposure was measured using a chromatographic assay, and the percent decrease is listed below:
   Formulation of Example 1: 28.5% decrease.
   Formulation of Example 2: 0.7% decrease.
Results The use of meglumine as an excipient in sodium laquinimod prevented oxidation-related degradation of laquinimod sodium under forced conditions.

Example 4

Laquinimod Sodium Formulations Comprising Antioxidants or Chelating Agents

Laquinimod Sodium formulations are prepared using the process described in Example 2 with the use of antioxidants in the place of meglumine, or in addition to meglumine in the following proportions:

TABLE 3

| Oxidation Reducing Agent | % of formulation |
| --- | --- |
| Ascorbyl palmitate | 0.01-1 |
| Sodium or Potassium metabisulfite | 0.01-1 |
| Sodium or Potassium sulfite | 0.01-1 |
| Alpha tocopherol or derivatives thereof | 0.001-0.05 |
| Sodium ascorbate | 0.01-1 |

TABLE 3-continued

| Oxidation Reducing Agent | % of formulation |
| --- | --- |
| Disodium edetate | 0.005-1 |
| BHA (butylated hydroxyanisole) | 0.001-0.1 |
| BHT (butylated hydroxytoluene) | 0.001-0.1 |
| Propyl gallate | 0.002-0.1 |

Example 5

Laquinimod Sodium Formulations Packaged in Containers with Oxygen Absorbing Agent An oxygen absorbing agent is a material that removes oxygen from a closed container by reacting with it chemically to bind it.

A preferred example of an oxygen absorbing agent is iron, preferably in powdered form. In a sealed container, the oxygen absorbing agent maintains the oxygen content of the air in the headspace of the container at a level preferably lower than 10%, and most preferably, lower than 1%.

Other metals which can be used include nickel, tin, copper and zinc.

Examples of oxygen absorbers have been disclosed in US Application Publication Number US 2007/0163917.

Laquinimod sodium formulations are packaged in closed containers containing oxygen absorber and in closed containers without oxygen absorbers. After a month, the amount of laquinimod is determined in the formulations in both containers.

Oxygen absorbers can be useful in lowering the amount of oxygen-based degradation in the laquinimod formulations.

Example 6

Laquinimod Sodium Formulations Packaged in Oxygen Impermeable Containers

Laquinimod Sodium Formulations are packaged in containers sealed in an oxygen-free or in a reduced-oxygen environment. The formulations are stored for a month. The content of laquinimod in the formulations is compared to similar formulations which are packaged in standard non-oxygen-reduced environments.

Oxygen absorbers can be useful in lowering the amount of oxygen-based degradation in the laquinimod formulations.

Example 7

Coating of Laquinimod Tablets with an Oxygen-Proof Coating

Tablets are coated with a film coating which prevents contact of the atmosphere. The film does not significantly change the dissolution profile of the tablet, yet prevents contact of oxygen in the air within the packaging with the laquinimod in the tablet.

The coating may be a wax or a coating such as Opadry®fx™ manufactured by Colorcon, West Point, Pa., USA.

Coatings may be used on laquinimod tablets with meglumine, without meglumine, with antioxidants or without antioxidants.

Oxygen-proof coatings can be useful in lowering the amount of oxygen-based degradation in the laquinimod formulations.

Example 8

Oxidation-Derived Impurities in Laquinimod Pharmaceutical Compositions

The following table includes compounds which may be present in pharmaceutical compositions comprising laquinimod in small quantities as a result of oxidation of laquinimod.

TABLE 4

| | |
|---|---|
| 2-Chloro-6-(1-ethyl-N-methyl-2-oxoindoline-3-carboxamido) benzoic acid (Compound I) | 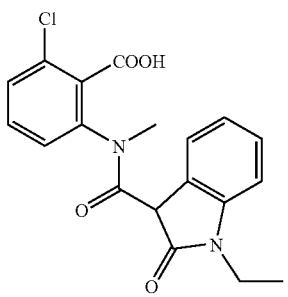 |
| 1H,3H-spiro[5-chloro-1-methylquinoline-2,4-dione-3,3'-[1]ethylindolin-[2]-one] (Compound II) | 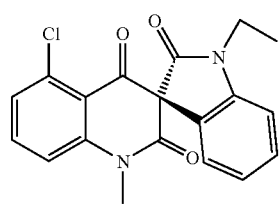 |
| 5-Chloro-N-ethyl-3-hydroxy-1-methyl-2,4-dioxo-N-phenyl-1,2,3,4-tetrahydro-quinoline-3-carboxamide (Compound III) | 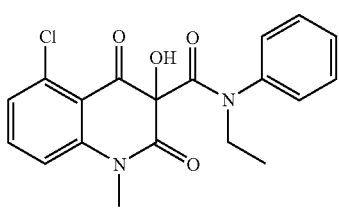 |

These oxidation products may be formed in the presence of laquinimod and oxygen. Factors which may increase the formation of these products include water and/or transition metal ions, which are in direct contact with the laquinimod, e.g. which are in the formulation.

Discussion

The use of meglumine reduces the degradation of the laquinimod sodium in a formulation. Specifically, when exposed to 0.15% $H_2O_2$ solution for 40 minutes the formulation with meglumine of Example 2 exhibited less than 2.5% of laquinimod sodium degradation as compared to an analogous formulation without meglumine under the same conditions. Meglumine appears to be acting to reduce the oxidation of laquinimod. Therefore, other methods for preventing or reducing oxidation, such as the methods described herein, may be used to reduce the oxidation of laquinimod and prevent or inhibit formation of oxidation degradation products. Such methods include formulating laquinimod with antioxidant, chelating agent, and/or reduction agent, as well as packaging methods, coating methods and/or processing methods designed to reduce oxidation.

To determine whether any given method for preventing or reducing oxidation is effective, known techniques may be employed to identify whether a laquinimod composition contains any one of Compound I, II, or III, or mixtures thereof.

Example 9

Preparation of Compound II

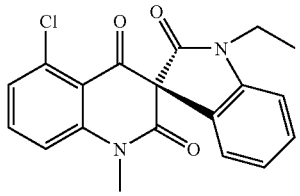

Laquinimod (14.01 mmol, 5.00 g), CAN (28.02 mmol, 15.4 g), ethanol (99.5%, 50 ml), and acetic acid (5.0 ml) were stirred at ambient temperature for 1 hour and water (30 ml) was then added. After stirring for 10 min the precipitate was collected by filtration, washed with water, then washed with cold ethanol (99.5%), and dried to yield the spiro Compound II (4.73 g, 95%).

Example 10

Preparation of Compound I

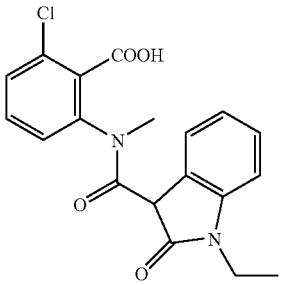

The Compound II from Example 9 (5.15 mmol, 1.83 g) was stirred in a mixture of 1M NaOH (10.0 mmol, 10.0 mL) and 1,4-dioxane (4 mL) at room temperature for 2 h and then diluted with water (30 mL). The mixture was acidified with 5 M HCl to pH 1, stirred for 15 min and the precipitate was collected, washed with water and dried to afford Compound I (1.73 g, 90% yield). When Compound I is heated in ethanol the molecule decomposes into 2-methylamino-6-chloro benzoic acid and 1-ethyl-2-oxo-2,3-dihydro-1H-indole-3-carboxylic acid ethyl ester. Compound I is purified by dissolution in a mixture of ethanol and aqueous 1 M NaOH and precipitation at room temperature by addition of HCl.

Example 11

Preparation of Compound III

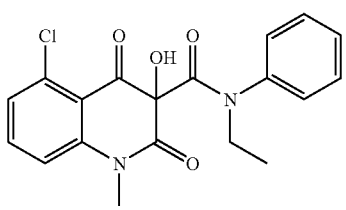

Sodium salt of 5-Chloro-N-ethyl-1,2-dihydro-4-hydroxy-1-methyl-2-oxo-N-phenyl-3-quinolinecarboxamide (1.00 g, 2.64 mmol) was added to a mixture of disodium hydrogenphosphate dehydrate (1.15 g, 6.4 mmol), Oxone (2KHSO$_3$.KHSO$_4$.K$_2$SO$_4$, 1.97 g, 3.20 mmol), and water (20 ml), and was stirred for 30 minutes. The resulting precipitate was collected, washed with ethanol/water 2:8, and dried to give Compound III (939 mg, 95%). K. Jansson et al. "Synthesis and Reactivity of Laquinimod, a Quinoline-3-carboxamide: Intramolecular Transfer of the Enol Proton to a Nitrogen Atom as a Plausible Mechanism for Ketene Formation", J. Org. Chem. 2006, 71, p 1667.

Example 12a

Experiments of Laquinimod Na with Antioxidants

Two wet granulations were prepared from Laquinimod Na, mannitol, lactose and water (Batches 1 and 2). One batch (Batch 1) did not contain antioxidants Butylated hydroxytoluene (BHT) and Butylated hydroxyanisole (BHA). For the other batch (Batch 2), the antioxidants (BHT and BHA) were dissolved in EtOH and added to the granulate.

The granulates were dried and milled. For both batches, 10% of Crospovidone was added and mixed for 15 minutes and then Pruv® was added and mixed for 5 minutes. The final blends were tested for non-Polar IDD (3-HLAQ) (Compound III). The compositions of batches 1 and 2 and the resulting percent 3-HLAQ (Compound III) impurity relative to Laquinimod are shown in Table 5. The impurities were detected before storage at accelerated conditions.

TABLE 5

|  | 1 | 2 |
|---|---|---|
|  | Quantity (mg) | |
| Laquinimod Na | 0.64 | 0.64 |
| Mannitol | 70.00 | 70.00 |
| Lactose M. | 70.00 | 70.00 |
| BHT | — | 0.028 |
| BHA | — | 0.028 |
| Pruv ® | 1.50 | 1.50 |
| Crospovidone | 10% | 10% |
| 3-HLAQ (%) | 0.34 | 0.15 |

Example 12b

Experiments of Laquinimod Na with Antioxidants

Two batches of wet granulations were prepared from Laquinimod Na, mannitol, lactose, Povidone K-30 and water.

In one batch (Batch 3), the granulate was dried and milled. Then 0.1% Pruv® was added and mixed for 5 minutes. The final blend was tested for non-Polar IDD (3-HLAQ) (Compound III).

In the other batch (Batch 4), antioxidants (BHT, BHA and Propyl Gallate) were dissolved in EtOH and added to granulate. The granulate was dried and milled. The blend was tested for non-Polar IDD (3-HLAQ) (Compound III). The impurities were detected before storage at accelerated conditions.

The compositions of each batch and resulting percent 3-HLAQ (Compound III) impurity relative to Laquinimod are shown in Table 6.

TABLE 6

|  | 3 | 4 |
|---|---|---|
|  | Quantity (mg) | |
| Laquinimod Na | 0.64 | 0.64 |
| Mannitol | 70.00 | 70.00 |
| Lactose M. | 70.00 | 70.00 |
| Povidone K-30 (10%) | 14.00 | 14.00 |
| BHT | — | 0.028 |
| BHA | — | 0.028 |
| Propyl Gallate | — | 0.185 |
| Pruv ® | 1.50 | — |
| 3-HLAQ (%) | 1.39 | 0.77 |

Discussion

Experiments 12a and 12b show that antioxidants limited impurity formation and reduced the percent of degradation product 3-HLAQ (Compound III) relative to Laquinimod.

What is claimed is:

1. A process for validating a batch of a pharmaceutical product containing N-ethyl-N-phenyl-1,2,-dihydro-4-hydroxy-5-chloro-1-methyl-2-oxoquinoline-3-carboxamide or a salt thereof and a pharmaceutically acceptable carrier for distribution comprising
   a) subjecting a sample of the batch to stability testing;
   b) determining the total amount of an oxidation decomposition product in the sample of the batch after stability testing; and
   c) validating the batch for distribution only if the sample of the batch after stability testing contains not more than a total of 0.5% w/w relative to N-ethyl-N-phenyl-1,2,-dihydro-4-hydroxy-5-chloro-1-methyl-2-oxoquinoline-3-carboxamide of the oxidation decomposition products of N-ethyl-N-phenyl-1,2,-dihydro-4-hydroxy-5-chloro-1-methyl-2-oxoquinoline-3-carboxamide,
   wherein the oxidation decomposition product is 2-Chloro-6-(1-ethyl-N-methyl-2-oxoindoline-3-carboxamido) benzoic acid, 5-Chloro-N-ethyl-3-hydroxy-1-methyl-2,4-dioxo-N-phenyl-1,2,3,4-tetrahydroquinoline-3-carboxamide or 1H,3H-spiro[5-chloro-1-methylquinoline-2,4-dione-3,3'-[1]ethylindolin-[2]-one], or a mixture thereof.

2. The process of claim 1, wherein in the step (b), the amount is determined using a measurement of mass, ultraviolet absorption, refractive index, ionization or voltammogram.

3. The process of claim 1, wherein the N-ethyl-N-phenyl-1,2,-dihydro-4-hydroxy-5-chloro-1-methyl-2-oxoquinoline-3-carboxamide is in the form of a pharmaceutically acceptable salt.

4. The process of claim 3, wherein the pharmaceutically acceptable salt of N-ethyl-N-phenyl-1,2,-dihydro-4-hydroxy-5-chloro-1-methyl-2-oxoquinoline-3-carboxamide is a lithium salt, a sodium salt or a calcium salt.

5. The process of claim 3, wherein the pharmaceutically acceptable salt of N-ethyl-N-phenyl-1,2,-dihydro-4-hydroxy-5-chloro-1-methyl-2-oxoquinoline-3-carboxamide is N-ethyl-N-phenyl-1,2,-dihydro-4-hydroxy-5-chloro-1-methyl-2-oxoquinoline-3-carboxamide sodium.

6. A process for validating a batch of a pharmaceutical product containing N-ethyl-N-phenyl-1,2,-dihydro-4-hydroxy-5-chloro-1-methyl-2-oxoquinoline-3-carboxamide or a salt thereof and a pharmaceutically acceptable carrier for distribution comprising
   a) subjecting a sample of the batch to stability testing;
   b) determining the total amount of an oxidation decomposition product in the sample of the batch after stability testing; and c) validating the batch for distribution only if the sample of the batch after stability testing contains not more than a total of 0.1% w/w relative to N-ethyl-N-phenyl-1,2,-dihydro-4-hydroxy-5-chloro-1-methyl-2-oxoquinoline-3-carboxamide of the oxidation decomposition products of N-ethyl-N-phenyl-1,2,-dihydro-4-hydroxy-5-chloro-1-methyl-2-oxoquinoline-3-carboxamide, wherein the oxidation decomposition product is 2-Chloro-6-(1-ethyl-N-methyl-2-oxoindoline-3-carboxamido) benzoic acid, 5-Chloro-N-ethyl-3-hydroxy-1-methyl-2,4-dioxo-N-phenyl-1,2,3,4-tetrahydro-quinoline-3-carboxamide or 1H,3H-spiro[5-chloro-1-methylquinoline-2,4-dione-3,3'-[1]ethylindolin-[2]-one], or a mixture thereof.

7. The process of claim 6, wherein in the step (b), the amount is determined using a measurement of mass, ultraviolet absorption, refractive index, ionization or voltammogram.

8. The process of claim 6, wherein the N-ethyl-N-phenyl-1,2,-dihydro-4-hydroxy-5-chloro-1-methyl-2-oxoquinoline-3-carboxamide is in the form of a pharmaceutically acceptable salt.

9. The process of claim 8, wherein the pharmaceutically acceptable salt of N-ethyl-N-phenyl-1,2,-dihydro-4-hydroxy-5-chloro-1-methyl-2-oxoquinoline-3-carboxamide is a lithium salt, a sodium salt or a calcium salt.

10. The process of claim 8, wherein the pharmaceutically acceptable salt of N-ethyl-N-phenyl-1,2,-dihydro-4-hydroxy-5-chloro-1-methyl-2 oxoquinoline-3-carboxamide is N-ethyl-N-phenyl-1,2,-dihydro-4-hydroxy-5-chloro-1-methyl-2-oxoquinoline-3-carboxamide sodium.

11. The process of claim 5, wherein the oxidation decomposition product is 2-Chloro-6-(1-ethyl-N-methyl-2-oxoindoline-3-carboxamido) benzoic acid.

12. The process of claim 5, wherein the oxidation decomposition product is 5-Chloro-N-ethyl-3-hydroxy-1-methyl-2,4-dioxo-N-phenyl-1,2,3,4-tetrahydro-quinoline-3-carboxamide.

13. The process of claim 5, wherein the oxidation decomposition product is 1H,3H-spiro[5-chloro-1-methylquinoline-2,4-dione-3,3'-[1]ethylindolin-[2]-one].

14. The process of claim 10, wherein the oxidation decomposition product is 2-Chloro-6-(1-ethyl-N-methyl-2-oxoindoline-3-carboxamido) benzoic acid.

15. The process of claim 10, wherein the oxidation decomposition product is 5-Chloro-N-ethyl-3-hydroxy-1-methyl-2,4-dioxo-N-phenyl-1,2,3,4-tetrahydro-quinoline-3-carboxamide.

16. The process of claim 10, wherein the oxidation decomposition product is 1H,3H-spiro[5-chloro-1-methylquinoline-2,4-dione-3,3'-[1]ethylindolin-[2]-one].

* * * * *